United States Patent [19]

LeBeau

[11] Patent Number: 5,627,132
[45] Date of Patent: May 6, 1997

[54] METHOD AND COMPOSITION FOR PLANT PRESERVATION WITHOUT LEAF CURLING

[75] Inventor: Raoul J. LeBeau, East Brookfield, Mass.

[73] Assignee: Voyager Enterprises Inc., Leominster, Mass.

[21] Appl. No.: 554,457

[22] Filed: Nov. 7, 1995

[51] Int. Cl.$^6$ ........................................ A01N 3/02
[52] U.S. Cl. ........................................ 504/114
[58] Field of Search ........................ 504/114, 115

[56] References Cited

U.S. PATENT DOCUMENTS

| | | | |
|---|---|---|---|
| 3,000,722 | 9/1961 | Linnolt | 71/11 |
| 3,122,432 | 2/1964 | Biggs | 71/2.4 |
| 3,287,104 | 11/1966 | Biggs | 71/2.4 |
| 3,874,871 | 4/1975 | Sy et al. | 71/68 |
| 3,895,140 | 7/1975 | Sheldon et al. | 428/22 |
| 4,092,145 | 5/1978 | Willard, Sr. | 71/68 |
| 4,243,693 | 1/1981 | Nordh | 427/4 |
| 4,248,734 | 2/1981 | Romero-Sierra et al. | 252/400 |
| 4,278,715 | 7/1981 | Romero-Sierra et al. | 428/22 |
| 4,287,222 | 9/1981 | Robinson | 427/4 |
| 4,710,394 | 12/1987 | Sellegaard | 427/4 |
| 5,112,380 | 5/1992 | Yamamoto et al. | 426/321 |

FOREIGN PATENT DOCUMENTS

| | | |
|---|---|---|
| 0964197 | 3/1975 | Canada. |
| 969479 | 6/1975 | Canada. |
| 1103476 | 6/1981 | Canada. |
| 1150963 | 8/1983 | Canada. |

*Primary Examiner*—S. Mark Clardy
*Attorney, Agent, or Firm*—Timothy H. Joyce

[57] ABSTRACT

Living plants, in particular coniferous and deciduous woody plants, are preserved by having them take up a preservation solution containing water, glycerin, a phosphate (e.g., calcium phosphate at 1.2–1.8 grams per liter of solution) and a biochemical energy source (e.g., sucrose at 4.0–8.0 grams per liter of solution). The preservation composition or solution provides for a gradual and complete preservation of the plant without the problem of chemicals "bleeding" from the leaves or incomplete preservation. The original texture, color, and odor of the plant is maintained. Additional dyes or coloration may be used in the preservation process.

17 Claims, No Drawings

METHOD AND COMPOSITION FOR PLANT PRESERVATION WITHOUT LEAF CURLING

The present invention is directed generally to a method and composition for plant preservation and more specifically to a formula which uses glycerin, water, calcium phosphate and a sucrose solution to gradually preserve a plant without the loss of the plants original leaf structure or coloration.

Presently, there exist a variety of methods and compositions for treating and preserving plants, bushes, trees and woody type plants. Living plants have been preserved by having the plants take up a preservation liquid by means of the plants roots or a cut end of the plant which exposes the plants xylem and phloem tubes or sieve tubes. The process of photosynthesis and transpiration are used advantageously to draw the chemical composition up into the plant. Additionally, many of the methods of treatment which use such a procedure, use a chemical composition which includes glycerin and water, or combinations of chemicals with a glycerin and water treatment. Some of the chemical combinations use various dyes, inorganic salts, monohydric alcohols, sulfates, potassium nitrates or phosphates in the preservation solutions in addition or in place of the glycerin and water.

However, even though there may exist a variety of formulas to preserve plants, few methods and compositions have proven successful in maintaining the original integrity of the plant's color, odor and texture. Plant preservation has been largely limited to woody-type plants and has been far too limited and ineffective to warrant use of such methods and formulas for industrial manufacture. Moreover, the original plant's flexibility, coloration, and resilience have been lost by the plants in each of the prior art treatments. A still further limitation in such treatments is the fact that preservation must be, in many cases, carried out or performed during the summer months while the sap is rising in the plant during transpiration. These processes, therefore, take an unrealistically long period of time and provide an inadequate quality of preserved plant.

Further attempts have been made to increase the life of various plants by spraying them with a preparation which deposits an air impermeable membrane on the plant's leaf surface. Such methods have also proven ineffective due to the fact that it is virtually impossible to cover every plant completely and uniformly during the preservation process. The preservation of plants in this way generally causes the areas of the plant beneath such membranes to eventually dry out and set the natural degradation processes of the plant into motion. This obviously provides for a less than adequate preserved plant or product.

More recently, prior art methods and compositions have been developed which provide for a somewhat improved plant product using a formula of glycerin, water, and tartrazine dye. Such treatments claim the ability to preserve the plant to the outermost leaves or needles. This method has been particularly applied to the genuses Thuja, Pinus, Juniperus, Quercus, Fagus, Ilex, Chamaecyparis, Cupressus, Prunus, Hedera, Elaeagnus, and Mahonia. However, such preservation solutions are far from being effective in being utilized for production of plants for industrial or domestic use, because of the loss of plant coloration, incomplete preservation of the plant's leaf curling, or the "bleeding" of the chemicals and glycerin from the leaves or needles of the plants after the preservation process. The failure of such preservation techniques is probably caused by the lack of nutrients or energy sources for the plant to regulate the transpiration processes. This "bleeding" of chemicals is undesirable because the residue often causes an overall change in the coloration of the plant or provides a shiny and sticky yellow texture to the plant's leaf surface. In most cases, the plant's original coloration needs to be restored by the addition of further dyes or addition of other chemicals. These problems, therefore, substantially increase the cost of the prior art plant preservation processes. Methods and compositions for plant preservation would, therefore, be desirable which would preserve the plant to its leaf tips, yet not kill and destroy the plant immediately, so that active transport and the preservation process could gradually and thoroughly take hold on the plant through the plants natural transpiration processes. Additionally, such plant preservation methods and compositions should also maintain the original plant's coloration and not "bleed" through the plant's leaves.

These and other difficulties experienced with the prior art have been obviated by the present invention.

It is, therefore, an outstanding object of the present invention to provide a method and composition for plant preservation which preserves plants, but maintains the plants original color, texture and odor.

Another object of the present invention is the provision of a method and composition for plant preservation which is simple to use, cost effective and can be used with or without additional dyes.

A further object of the present invention is the provision of a method and composition of plant preservation which will maintain the plants original turgor, prevent degradation of the plant and not "bleed" out of the plant to the leaves surface.

A still further object of the invention is to provide a method and composition of plant preservation which will work with a variety of different plants during any time of the year.

Another object of the invention is the provision of a plant method and composition which will enhance the original coloration of the plant through the preservation process and work effectively on the majority of woody plants, evergreens, deciduous, and most grasses and cereals found in the wild in temperate North America which are suitable for decorative applications.

With the foregoing and other objects in view, which will appear as the description proceeds, the invention resides in the combination and arrangement of steps and the details of the composition hereinafter described and claimed, it being understood that changes in the precise embodiments of the invention herein disclosed, may be made within the scope of what is claimed without departing from the spirit of the invention.

SUMMARY OF THE INVENTION

The present invention relates to a method and composition of preservation of plants by a mixture glycerin, water, biochemical energy sources phosphates.

Basically, living plants may be preserved by causing the aspiration and transpiration of a mixture of glycerin, water, sucrose and calcium phosphate solution. The mixture or solution is added to the roots or cut end of the plant and then is allowed to enter the plant by absorption and is carried up through the plant by cohesion tension during the plants transpiration processes. The methodology and formula described provide for a preservation of woody plants for extended periods during which time the plant retains its natural characteristics and aesthetics without the need for further maintenance.

The use of calcium phosphate (1.2–1.8 grams per liter of solution) and sucrose (4.0–8.0 grams per liter of solution) in glycerin and water, provides for the superior and uniform preservation of the plant. The calcium phosphate and sucrose provide for a gradual and uniform preservation of the plant or plant material without the "bleeding" of the chemicals or glycerin and dye through the leaves stomatea and guard cells onto the leaves surface. The solution and method provides for a plant which can be easily manufactured for sale and which maintains the original coloration, texture, and odor of the original live plant.

DESCRIPTION OF THE PREFERRED EMBODIMENTS

Factors Affecting Stomatal Movements

A number of environmental factors affect stomatal opening and closing, water loss being the major influence. When the turgor of a leaf drops below a certain critical point, which varies with different species, the stomatal opening becomes smaller. The effect of water loss overrides other factors affecting the stomata, but stomatal changes can occur independently of overall water gain or loss by the plant. The most conspicuous example is found in the many species in which the stomata open regularly in the morning and close in the evening, even though there may be no changes in the amount of water available to the plant.

In many plants, there is a marked increase in the level of abscisic acid (ABA) during periods of water stress. When ABA is added to leaves it causes stomatal closure within a few minutes; moreover the effect of ABA is a reversible process and can be controlled. It is also important to note that solute ($K^+$) loss from guard cells begins when ABA of mesophyll origin arrives at the stomata, signaling the stomata that the mesophyll cells are experiencing water stress. Additionally, quantitative changes in potassium concentrations across stomatal complex (guard cells and subsidiary cells) have been measured. Evidence supports the proposition that there are significant changes in vacuolar potassium concentrations when the stomata are closed. In other words, when high concentrations of ($K^+$) are maintained in the guard cells there is a stronger likelihood that the guard cells will remain open. It, therefore, would be important in a plant preservation process to provide a source of ($K^+$) in a high enough concentration that the stomata remain open. This is important since the overall uptake of water or solutions by the plant is regulated by the plants overall transpiration processes. The overall transpiration process uses cohesion tension to draw water, sap or nutrients up into the plant. In a sense, a long chain of molecules are drawn up into the plant. Therefore, it is most desirable to provide a molecule which will provide hydrogen bonding during the transpiration process so that flow can be maximized throughout the plant. This is the reason that glycerin has been effective for plant preservation. It closely resembles water by its hydrogen bonding capabilities, but is more viscous than water and, therefore, can not be used by the plant metabolically. In this overall process it is increasingly important that transpiration in the plant continue during such a preservation process. This can be accomplished by ($K^+$) loading of the preservation solution in an appropriate ratio which is described in more detail below. The appropriate levels of ($K^+$) prevent the efflux of ($K^+$) ions from the guard cells and, therefore, prevent them from closing during the preservation process. This provides for maximum preservation of the plant or plant material. Secondly, it is true that environmental factors such as carbon dioxide, chemical concentration, light and temperature can cause stomatal closure. However, the concentration of ($K^+$) can be used to significantly influence the plant's guard cells to remain open during transpiration and while the plant is being preserved. Furthermore, the ATP pump which fuels the proton pumping of the guard cells will continue in operation until the energy sources are used up or not available. Few plant preservation techniques have been effective, because they lack the appropriate balance of ($K^+$) ions and energy sources. By providing ($K^+$) and sucrose (or a similar biochemical energy source) in the original glycerin preservation solution, the transpiration process can be maximized for full preservation of the plant. An appropriate concentration and type of energy source must be provided so that the ATP pump in the cell membrane of the guard cells can continue to function. After the energy source has been diminished, the plant begins to die and the stomata close due to the imbalances and efflux of the ($K^+$) ions. This provides for a perfect preservation of the plant and prevents the later "bleeding" of the chemicals from the plant's leaves through each of the small guard cells. The process and treatment can, therefore, be used in a variety of temperature and humidity conditions.

Water and Glycerin Transport: The Cohesion-tension Mechanism

Water or glycerin enter the plant by the roots or a cut stem. The general pathway in which the water or glycerin enters and circulates through the plant has been clearly identified. One can trace the pathway simply by placing a cut stem in water or glycerin that is colored with a dye (preferably the stem should be cut under the water to prevent air from entering the conducting element of the plants xylem) and then tracing the path of the liquid into the leaves. The dye or stain quite clearly delineates the conducting elements of the xylem. Experiments using radioisotopes confirm that the isotope and/or presumably the water and/or glycerin do indeed travel by way of the vessel elements (tracheids) in the xylem. How the water and/or glycerin solution moves thorough the plant is a second issue which is worthy of further discussion.

When water evaporates from the cell wall surfaces bordering the intercellular spaces in the interior of a leaf during transpiration, it is replaced by water form within the cell. This water diffuses across the plasma membrane, which is freely permeable to water, but not to the solutes of the cell. This point is important for obtaining appropriate plant preservation with the present formula. As a result, the concentration of solutes within the cell increases and the water potential of the cell decreases. A gradient of water potential then becomes established between this cell and adjacent, more saturated cells. These cells in turn, gain water and/or glycerin from other cells until eventually this chain of events reaches a maximum and exerts a "pull", or tension, on the water or glycerin in the xylem. Because of the extraordinary cohesiveness of the glycerin and/or water molecules, this tension is transmitted all the way down to the stem or cut end of the plant which has been submerged in a bath or suitable container. The water and glycerin solution is withdrawn from the bath, pulled up the xylem in a steady and gradual process during transpiration, and distributed to the cells that are losing water vapor through the stomata openings to the atmosphere. This water loss makes the potential at the cut end or roots of the plant, more negative and increases the capacity of the system to extract the solution from the bath. Hence, the lower water potential at the leaves, brought about by transpiration and/or by the use of water in the leaves, results in a gradient of water potential from the leaves to the cut end or roots of the plant. This gradient of water and water/glycerin provides for the driving force for the gradual and systematic movement and preservation of the plant. It is, therefore, important what chemicals and concentrations are used in the preservation solution. For instance, if too little glycerin is used there could be no preservation of the plant or incomplete preservation. Furthermore, if too much glycerin is used in the preservation solution, it is likely that the cohesion tension in the plant could not be strong enough to uptake a very viscous fluid. Appropriate solution concentrations, therefore, will prevent the bane of the cohesion tension mechanism which is the filling of vessels and tracheids with air. Embolized tracheal elements can not conduct water and the plant will die without proper preservation with the glycerin/water solution.

Uptake of Inorganic Nutrients

The uptake or absorption, of inorganic ions takes place through the epidermis of the plant. Current evidence suggests that the major pathway followed by ions from the epidermis to the endodermis of the root is symplastic. Ion uptake by the symplastic route begins at the plasma membrane of the epidermal cells. The ions then move from the epidermal cell protoplasts to the first layer of cortical cells (and possibly the exodermis) though the plasmodesmata in the epidermal cortical cell walls. Radial movement of ions continues in the conical symplast—from protoplast to protoplast via plasmodesmata—through the endodermis and into the parenchyma cells of the vascular cylinder by diffusion, possibly aided by cytoplasmic streaming within the individual cells. However, in areas of the plant such as the roots and leaves, the mineral concentrations and ions are much different than that of the medium in which the plant grows. Most importantly, since substances do not diffuse against a concentration gradient, it is clear that minerals are absorbed and distributed throughout the plant by means of active transport. Indeed the uptake of minerals is known to be an energy requiring process. For instance, if the roots of the plant are deprived of oxygen, or poisoned so that respiration is curtailed, mineral uptake and transport are drastically decreased. Also, if a plant is deprived of light or other needed mineral or energy sources, it will cease to transport salts or other inorganic nutrients after its carbohydrate reserves are depleted. Hence, ion transport through the xylem of the plant requires two active, carrier-mediated membrane events: 1) uptake at the plasma membrane of the epidermal cells at the source of the plant's cut end or roots and 2) secretion into the vessels at the plasma membrane of the parenchyma cells bordering the vessels. For this reason an appropriate energy source such as sucrose must be introduced into the preservation solution. Otherwise, these carrier mediated transport proteins and cells will cease to operate and an incomplete or poor plant product will result after or during preservation. The overall energy source, however, is important since the plant needs to be able to immediately and readily utilize the energy source without having to use and catabolize chemically complicated molecules and processes. As mentioned earlier it is these active transport processes which will maintain the appropriate conditions to provide for a complete and thorough preservation of the plant. Sucrose provides an excellent energy source during the preservation process because of it simple chemical structure. It is also a natural energy source used by most plants.

Transport of Inorganic Nutrients

Once secreted into the xylem vessels (or tracheids), the inorganic ions are rapidly transported upward and throughout the plant in the transpiration stream. Some ions move laterally from the xylem into surrounding tissues of the roots and stems, while others are transported into the leaves.

Much less is known about the pathways followed by ions in leaves than about those in roots. Within the leaves, the ions are transported along with the water in the leaf apoplast, that is, in the cell walls. Some ions may remain in the transpiration stream and reach the main regions of water loss; the stomata and other epidermal cells. Most ions eventually enter the protoplasts of the leaf cells, probably by carrier mediated transport mechanisms similar to those in roots. The ions may then move symplastically to other parts of the leaf, including the phloem.

Substantial amounts of the inorganic ions that are imported into the leaves through the xylem are exchanged with the phloem of the leaf veins and exported from the leaf together with sucrose in the assimilate, or translocation, stream. In preserving plants, it is, therefore, important to use sucrose or a similar type of energy source to diminish such export from the plant's leaves. For instance, in the annual white lupine (*Lupinus albus*), transport in the phloem accounts for more than 80 percent of the plants vascular intake or nitrogen and sulfur and at least 70 percent of its phosphorus, potassium, magnesium and zinc intake. The uptake by such plants is undoubtably coupled to the flow of sucrose or similar energy sources in the phloem.

Recycling may occur in the plant as nutrients reaching the roots in the descending assimilate stream of the phloem are transferred to the ascending transpiration stream of the xylem. Only those ions which can move in the phloem (i.e. phloem mobile ions), can be exported from the leaves to any extent. For example, ($K^+$), ($Cl^-$), and ($HPO_4^{2-}$) are readily exported from the leaves, whereas ($Ca^{2+}$) is not. Solutes such as calcium are said to be phloem immobile. For this reason we utilize calcium phosphate in our preservation solution. The calcium is taken up through the plant to the areas in which it will be used in the plant. The calcium is immobile to export and, therefore, is used to stabilize fluctuations of the ($K^+$) out of or into the plants cells. This is accomplished by the fact that the calcium is an immobile-phloem ion. This prevents the closure of the stomata and maintains the transpiration process for the complete replacement of water by the glycerin solution.

Mechanism of Phloem Transport and Pressure Flow

Briefly stated, the pressure-flow hypothesis is the leading theory regarding how assimilates are transported from sources to sinks along a gradient of turgor pressure developed osmotically. The present invention capitalizes on this theory. For example, sucrose produced by photosynthesis in a leaf is actively secreted into the sieve tubes of the minor veins of the plant. This active process called phloem loading, decreases the water potential in the sieve tube and causes water entering the leaf in the transpiration stream to move into the sieve tube by osmosis. With the movement of water into the sieve tube at this source, the sucrose is carried passively by the water to a sink, such as growing tissue, or a storage root, where the sucrose is removed and unloaded from the sieve tube. The removal of sucrose results in an increased water potential in the sieve tube at the sink and subsequent movement of water out of the sieve tube there. The sucrose may be either utilized in respiration or growth or stored at the sink, but most of the water returns to the xylem and is recirculated in the transpiration stream. It is this pressure flow hypothesis that casts the sieve tubes in a passive role in the movement of the sugar solution through them. Active transport is also involved in the pressure-flow mechanism; however, active transport is not directly involved with the long distance transport through the sieve tubes, but rather with loading and possibly unloading of sugars and other substances into and out of the sieve tubes. It is for this reason that sucrose has been added to the present invention so as to maximize the uptake of glycerin to the outermost areas of the plant's leaves. Furthermore, considerable evidence indicates that the driving force for sucrose accumulation (phloem loading) at the source is provided by a proton pump that is energized by ATP and mediated by and ATPase at the plasma membrane, and involves a sucrose-proton co-transport (symport) system. The metabolic energy required for loading and unloading may be expended entirely by companion cells or parenchyma cells bordering the sieve tubes, rather than by the sieve tubes. Until recently, it was assumed that loading occurred across the plasma membrane of the companion cells, which then transferred the sugar to its associated sieve tube via the many plasmodesmata connections in theft common wall. It now appears, however, that some sieve tubes are capable of loading themselves; the site of active transport being their own plasma membrane. Whatever the case, the mature sieve tube probably is dependent upon companion cells for much or most of its energy needs. By adding sucrose to our glycerin solution we are able to maintain the integrity of the plants active transport system. Furthermore, this situation is distinguished from a natural plant because sucrose is generally not found with such high concentrations in the xylem of the plant. Our preservation solution uses sucrose loading in the xylem so as to draw the water present in the plant from the phloem to the xylem, so that the water can be transpired out of the plant and the glycerin can replace the water in the phloem. Also, the sucrose loading or xylem loading provides for an energy source for both the sieve tube's companion cells and the parenchyma cells. This provides for the thorough and gradual preservation of the plant. Also, since the water in drawn into the xylem of the plant and transpired, the stomata stay open for a longer period of time. This full process provide for the improved plant preservation in which the original plant's odor, color and texture are preserved with little "bleeding" of chemicals from the plant's leaves.

The methodology and formulae described herein provide the rationale for, and the description of, a procedure for the preservation of woody plants for extended periods during which time the plants retain their natural characteristics and provide the aesthetics of living plants without the need for any type of maintenance.

In order for these procedures to proceed in a logical and reproducible manner, the following conditions should be maintained for optimizing the quality of the final preserved plant product:

1. The raw material (plants) should be fleshly cut on the day of processing and final cutting completed before immersion in the preservative solutions. The actual cutting of the plants should be done under water in order to prevent the formation of emboli in the xylem of the plant. Such emboli are known to destroy the plants free circulation and hamper the preservation of the plant. In such instances, the drying of the material following harvesting has resulted in inconsistent processing, leaf curling, and consequent loss of marketable product.

2. The chemical composition of the preservative solution must be designed to create an osmotic gradient which will prevent a negative water potential in the leafy elements which would result in the loss of normal turgor with subsequent deformation of leaf structure. The proposed invention provides a preservative solution intended to maintain the viability of the plant material during the course of the preservation treatment.

3. Sufficient ambient circulation of moderately dry air should be maintained in order to insure optimum transpiration through leaf systems and to maintain sufficient hydrostatic tension throughout the entire plant. Since the movement of water molecules through the vascular network is of prime importance to the process, and since transpiration through the stomata of the foliage provides the motive power for the movement, the circulation of the ambient air is important in maximizing the quality of the final plant product.

4. A temperature gradient is maintained between the upper section of the plant and the preservation solution. The differential is best if maintained in the order of 10 to 15 degrees Celsius. This gradient is also important in influencing the movement of inorganic ions into the phloem to allow for ionic movement into and out of the cellular elements.

5. The pH of the preservative solution should be adjusted to around 5.5+0.40 units. Absorption of the solution proceeds most rapidly under such conditions. Adjustment of the pH of the preservative solution has been inadequately described in past methodology and is presented here to provide additional quality control. The pH of the solution may be conveniently adjusted by the careful addition of a 10% sulfuric acid solution. The optimum pH environment for certain plants may be determined in order to prevent chemical trauma or premature death of plants during processing.

6. The color of the preserved plant material may be modified by the addition of various dyes. Such additive dyes should be chosen from among those which will provide the desired color in an acid environment.

The following basic formula and tests are presented as representative of the chemical composition needed for successful preservation of the most commonly desired decorative plant products. Although designed for use with woody plants, it is to be understood that the methodology presented, may be modified to include the treatment of many other species depending on the interest of the user. The dyes presented may also be modified to obtain various colors. The preservative solution should include the ionic composition needed to insure the viability of the plants during the preservation process. Care must be taken that active transport mechanisms are maintained as well as passive transport which regulates water mobility.

The following is a basic formula used for plant preservation:

| | |
|---|---|
| Potassium sulfate | 8.0 g |
| Sodium nitrate | 4.0 g |
| Oxalic acid | 0.75 g |
| Magnesium carbonate | 0.50 g |
| Calcium phosphate (monobasic) | 1.5 g |
| Sucrose | 4.0 g |

The above chemicals were added to 275 mL's of glycerin and 725 mL's of water to make a complete 1 liter solution. The above formula and the following examples are effective on the majority of woody plants, either evergreen or deciduous, and on most grasses and cereals. In contrast to other methods in the prior art, this formula and its modifications are effective at any time during the active growing cycles of the plant. This preservation formula has proven effective and suitable to preserve the following species and their subspecies:

| | |
|---|---|
| *Acacia Floribunda* | Pyracantha |
| Acer | Pseudotsuga |
| Arbutus | Quercus |

| | |
|---|---|
| Arundo | Rhamnus |
| Berberis | Rosmarinus |
| Betula | Salix |
| Carpinus | Santolina |
| Castanea | Sequoiadendron |
| Calycanthus | Spartium |
| Choisya | Thuya |
| Cotoneaster | Astilbe |
| Crytomeria | Cupressus |
| Cupressocyparis | Achillee |
| Cytisus | *Asparagus Acutilolius* |
| Eleagnus | Bambou |
| Escallonia | Bruyere |
| Eucalyptus | Cortaderia |
| Fagus | Erygium |
| Forsythia | Graminees |
| Genista | Gypsophile |
| Hedera | Myrte |
| Hypercium | *Palmes Phoenix* |
| Ilex | *Palme Washingtonia* |
| Juniperus | Papyrus |
| Lavadula | Sophora |
| Ligustrum | Typha |
| Liquidabar | Statice |
| Lonicera | Mahonia |
| Magnolia | Pinus |
| Platanus | Prunus |
| Populus | Arundo |
| Bouleau | Charme |
| Tsuga | Kalmia |
| Laurus | Larix |
| Cercidiphyllum | Syringa |
| Filicinae | Lavendulak |
| Rumex | Oxalis |
| Triticum | Achillea |

The following examples are presented as an illustration of the process and formula of the present invention and are not intended as an undue limitation on the broad scope thereof.

EXAMPLE #1

The following test was conducted using a circulating water bath maintained at 34 degrees Celsius. The treated plants included: Juniper, Popular, and Maple which were cut to 12" by 18" in length and placed in the treatment vessels. Plants were allowed to take up the solution for 72 hours (3 days). The plants were then hung upside down at the same ambient temperature conditions so that they could dry. The texture of the plants was very good and the preservation was completely out to the leaf tips. The plants did not "bleed" the chemical solution and maintained a high quality color and odor. The preservation solution was made up to 1 liter and included:

| | |
|---|---|
| Potassium sulfate | 8.01 grams |
| Sodium nitrate | 3.90 grams |
| Oxalic acid | 0.76 grams |
| Magnesium carbonate | 0.50 grams |
| Calcium phosphate (monobasic) | 1.50 grams |
| Sucrose | 4.00 grams |
| Acid blue | 0.40 grams |
| Acid yellow | 2.00 grams |
| Glycerine | 250 mL |
| $H_2O$ | 750 mL |

The overall color of the plants was a natural green which did not fade.

EXAMPLE #2

In this case, Blue Berry Juniper, Wild Sage, and Maple were treated with a preservation formula having:

| | |
|---|---|
| Potassium sulfate | 8.01 grams |
| Sodium nitrate | 4.20 grams |
| Oxalic acid | 0.00 gams |
| Magnesium carbonate | 0.52 grams |
| Calcium phosphate (monobasic) | 1.53 grams |
| Sucrose | 4.10 grams |
| Acid blue | 0.40 grams |
| Acid red | 2.00 grams |
| Glycerine | 250 mL |
| $H_2O$ | 750 mL |

The original plants were cut while submerged in a 34 degree Celsius water bath holding 1 liter of the above described chemicals. The ambient air temperature was maintained at 21 degrees Celsius and the plants were allowed to take up the solution for 72 hours (3 days). The plants were allowed another 5 days to take up the preservation solution and then were hung upside down to dry for 2 weeks. The final plants showed a superb rich maroon color and have remained supple, pliable and aromatic. The plants did not "bleed" the dye or chemicals.

EXAMPLE #3

In this case, one 7' 6"" Birch tree was treated with a preservation formula having:

| | |
|---|---|
| Potassium sulfate | 8.00 grams |
| Sodium nitrate | 4.01 grams |
| Oxalic acid | 0.75 grams |
| Magnesium carbonate | 0.50 grams |
| Calcium phosphate (monobasic) | 1.50 grams |
| Sucrose | 4.00 grams |
| Acid blue | 0.56 grams |
| Acid yellow | 2.82 grams |
| Glycerine | 250 mL |
| $H_2O$ | 750 mL |

The original plants were cut while submerged in a 30 degree Celsius water bath holding 1 liter of the above described chemicals. The ambient air temperature was maintained at 20 degrees Celsius and the plants were allowed to take up the solution for 72 hours (3 days). The one liter dose of the above formula was readily taken up by the tree. The one liter dose was not adequate to completely preserve the plant, so an additional 2.5 to 3.0 liters was added to the bath to insure complete preservation. The plant appeared to take up another 2.5 liters and then stopped. Leaves were not curled and showed a perfect natural color. Some leaves were then removed and examined under magnification to determine whether complete absorption had taken place in the transpiration process. There was no "bleeding" of chemicals onto the plant's leaves. The overall quality and texture of the plant was as if the tree were still alive.

EXAMPLE #4

In this case, a 6 foot maple tree with a diameter of 1.25" was treated with a preservation formula having:

| | |
|---|---|
| Potassium sulfate | 8.03 grams |
| Sodium nitrate | 4.01 grams |
| Oxalic acid | 0.78 grams |
| Magnesium carbonate | 0.51 grams |
| Calcium phosphate (monobasic) | 1.53 grams |
| Sucrose | 4.06 grams |
| Acid red | 1.05 grams |

| | |
|---|---|
| Acid yellow | 4.50 grams |
| Glycerine | 275 mL |
| $H_2O$ | 725 mL |

The original tree was cut while submerged in a 31 degree Celsius water bath holding 1 liter of the above described chemicals. The ambient air temperature was maintained at 20 degrees Celsius and the tree was allowed to take up the solution for 4 days. After the plant took up the first liter of solution a second liter was prepared and added to the water bath for the plant to take up. The plant appeared to take up about 1.5 liters of the preservation solution. The final preserved tree showed a superb rich mauve color and has remained supple, pliable and aromatic.

EXAMPLE #5

In this case, Henoki Cypress, Day Lilly, Juniper and Yarrow Goldenrod were treated with a preservation formula having:

| | |
|---|---|
| Potassium sulfate | 8.00 grams |
| Sodium nitrate | 4.01 grams |
| Oxalic acid | 0.80 grams |
| Magnesium carbonate | 0.52 grams |
| Calcium phosphate (monobasic) | 1.50 grams |
| Sucrose | 4.12 grams |
| Acid blue | 0.60 grams |
| Acid yellow | 2.80 grams |
| Glycerine | 250 mL |
| $H_2O$ | 750 mL |

The original plants were cut while submerged in a 30 degree Celsius water bath holding 1 liter of the above described chemicals. The ambient air temperature was maintained at 20 degrees Celsius and the plants were allowed to take up the solution for 72 hours (3 days). The final plants showed a superb rich color and have remained supple, pliable and aromatic.

EXAMPLE #6

The following formula has proven useful for treating conifers:

| | |
|---|---|
| Potassium sulfate | 20 grams |
| Sodium nitrate | 10 grams |
| Oxalic acid | 1.5 grams |
| Magnesium carbonate | 0.5 grams |
| Calcium phosphate (monobasic) | 1.5 grams |
| Sucrose | 4.0 grams |

The above formula was prepared in a similar type of water glycerin solution as mentioned above. The plants were placed in a water bath at 30 degrees Celsius and were allowed to take up the solution for 5 days. The room temperature was maintained at 22 degrees Celsius, for drying.

While it will be apparent that the illustrated embodiments of the invention herein disclosed are calculated adequately to fulfill the objects and advantages primarily stated, it is to be understood that the invention is susceptible to variation, modification, and change within the spirit and scope of the subjoined claims.

The invention having been thus described, what is claimed as new and desired to secure by Letters Patent is:

1. A plant preservation solution, comprising:
   (a) a solution of glycerin and water;
   (b) a simple sugar;
   (c) a phosphate;
   (d) an inorganic molecule selected from the group consisting of potassium sulfate, sodium nitrate, oxalic acid, and magnesium carbonate.

2. A plant preservation solution as recited in claim 1, wherein said simple sugar is sucrose.

3. A plant preservation solution as recited in claim 2, wherein said sucrose additive is from 4.0 to 8.0 grams per liter of solution.

4. A plant preservation solution as recited in claim 1, wherein said phosphate is calcium phosphate.

5. A plant preservation solution as recited in claim 4, wherein said phosphate is from 1.2 to 1.8 grams per liter of solution.

6. A plant preservation solution, comprising:
   (a) a solution of glycerin and water;
   (b) an energy source for maintaining said plants metabolism during the plant preservation process; and
   (c) at least one inorganic ion for regulating said plants stomata and guard cells activity during the transpiration and preservation processes.

7. A plant preservation solution as recited in claim 6, wherein said energy source is a carbohydrate.

8. A plant preservation solution as recited in claim 6, wherein said energy source is a disaccharide.

9. A plant preservation solution as recited in claim 6, wherein said energy source is a monosaccharide.

10. A plant preservation solution as recited in claim 6, wherein said energy source is an aldose.

11. A plant preservation solution as recited in claim 6, wherein said energy source is a ketose.

12. A plant preservation solution as recited in claim 6, wherein said inorganic ion is a macro-nutrient of said plant.

13. A plant preservation solution as recited in claim 6, wherein said inorganic ion is a micro-nutrient of said plant.

14. A method of preserving a plant, comprising the steps of:
   (a) preparing a preservation solution having glycerin, water, phosphate and a biochemical energy source as its components;
   (b) immersing said plant in the preservation solution of (a);
   (c) cutting said plant while immersed in said preservation solution;
   (d) allowing said plant to take up said preservation formula by its natural transpiration processes;
   (e) allowing said plant to dry after said preservation formula has been taken up into said plant.

15. A method of preserving plants, as recited in claim 14, wherein a dye may be added to said preservation solution to add to the overall aesthetic quality of the final preserved plant.

16. A method of preserving plants, as recited in claim 15, wherein the air temperature of the room is maintained at a temperature gradient range of from 10 to 15 Celsius degrees.

17. A method of preserving plants, as recited in claim 15, wherein sufficient ambient circulation of dry air is maintained in order to insure optimum leaf transpiration and uptake of the preservation formula.

* * * * *